United States Patent
Vachon

(10) Patent No.: US 6,475,196 B1
(45) Date of Patent: Nov. 5, 2002

(54) SUBCUTANEOUS INFUSION CANNULA

(75) Inventor: David J. Vachon, Granada Hills, CA (US)

(73) Assignee: MiniMed Inc., Sylmar, CA (US)

( * ) Notice: Subject to any disclaimer, the term of this patent is extended or adjusted under 35 U.S.C. 154(b) by 130 days.

(21) Appl. No.: 09/643,662

(22) Filed: Aug. 18, 2000

(51) Int. Cl.[7] .......................... A61M 5/32; A61M 25/00
(52) U.S. Cl. ........................................ 604/265; 604/132
(58) Field of Search .......................... 604/59, 132, 158, 604/285; 514/772.3

(56) References Cited

U.S. PATENT DOCUMENTS

| | | | | |
|---|---|---|---|---|
| 4,068,660 A | * | 1/1978 | Beck | 604/158 |
| 5,599,321 A | * | 2/1997 | Conway et al. | 604/265 |
| 5,756,553 A | * | 5/1998 | Iguchi et al. | 514/772.3 |
| 5,762,638 A | * | 6/1998 | Shaikani et al. | 604/265 |
| 5,810,769 A | * | 9/1998 | Schlegel et al. | 604/59 |
| 5,885,250 A | * | 3/1999 | Kriesel et al. | 604/132 |

\* cited by examiner

*Primary Examiner*—Teresa Walberg
*Assistant Examiner*—Leonid Fastovsky
(74) *Attorney, Agent, or Firm*—Gates & Cooper LLP

(57) ABSTRACT

Provided is an infusion cannula modified to incorporate one of more medicinal agents. The infusion cannula has a tube having an inner lumen and an external surface, and is made of a flexible, biologically compatible elastomeric material, with a coating adhered to the external surface of the tube. The coating contains a medicinal agent in a polymer matrix. Preferably, the polymer is capable of sustained release of the medicinal agent. The infusion cannula can be produced by coating a tube with a medicinal agent in a polymer matrix. In some embodiments, the coating involves dipping the tube into the polymer matrix, or spraying or painting the polymer matrix onto the tube. Additionally provided is a method for infusing a substance into a subject by inserting the cannula into subcutaneous tissue of the subject and delivering the substance into the cannula, thereby infusing the substance into the subject through the cannula.

20 Claims, 4 Drawing Sheets

SUBCUTANEOUS INFUSION CANNULA

TECHNICAL FIELD OF THE INVENTION

This invention relates generally to the manufacture and use of an infusion cannula suitable for subcutaneous implantation. The infusion cannula is capable of controlled release of an gent that facilitates maintenance of the infusion site.

BACKGROUND OF THE INVENTION

Subcutaneous infusion sets are generally known in the medical arts for use in the administration of a selected medication or other therapeutic fluid to a desired subcutaneous infusion site located beneath the skin of a patient. Such infusion sets typically include a tubular cannula or catheter that is supported by and protrudes from a compact housing adapted to receive the infusion fluid via delivery or infusion tubing, which is suitably connected to other components of the fluid infusion system. Infusion sets can be used, for example, to transport insulin from an insulin pump to a subcutaneous site in a patient.

The subcutaneous infusion set normally includes an insertion needle, which is assembled with the soft cannula and is adapted to pierce the patient's skin for transcutaneous cannula placement. The insertion needle is thereafter withdrawn to leave the cannula in place for subcutaneous fluid infusion. Exemplary subcutaneous infusion sets of this general type are described in U.S. Pat. Nos. 4,755,173; 5,176,662; and 5,257,980, which are incorporated by reference herein. Such subcutaneous infusion sets are commonly used with compact medication infusion pumps for programmable administration of medication such as insulin. Exemplary infusion pumps of this general type are described in U.S. Pat. Nos. 4,562,751; 4,678,408; and 4,685,903, which are incorporated by reference herein.

Although the material used for such cannulae are flexible enough to provide comfort for the patient, the inevitable movement of the cannula that occurs as a patient moves results in inflammation. Where a needle is inserted for cannula placement, an injury is created. The implanted cannula, a foreign body, elicits an exacerbated host response, while greater inflammation occurs as a result of any cannula movement. There remains a need, therefore, for improved cannula materials that will reduce irritation to the patient, reduced incidence of infection and reduced incidence of site loss through reduced host response (e.g., deactivation of macrophages and foreign body giant cells at the implant site).

SUMMARY OF THE INVENTION

To overcome the limitations in the prior art described above, and to overcome other limitations that will become apparent upon reading and understanding the present specification, the invention provides an infusion cannula modified to incorporate one or more medicinal agents. The infusion cannula comprises a tube having an inner lumen and an external surface. The tube comprises an elastomeric material, wherein the elastomeric material is preferably a flexible, biologically compatible material. The tube additionally comprises a coating adhered to the external surface of the tube, wherein the coating comprises a medicinal agent and a polymer matrix. In a preferred embodiment, the medicinal agent is embedded in the polymer matrix, and the polymer is capable of sustained release of the medicinal agent.

Examples of medicinal agents include, but are not limited to, anti-inflammatory, anti-bacterial, anti-viral and disinfecting agents, such as dexamethasone, cefazolin, acyclovir, and benzalkonium chloride. Examples of elastomeric materials include, but are not limited to, polyurethane, polyurea, polyether(amide), PEBA, thermoplastic elastomeric olefin, copolyester, and styrenic thermoplastic elastomer. In some embodiments, the coating further comprises a solvent system, such as tetrahydrofuran and/or isopropyl alcohol. In some embodiments, the tube has a gauge of about 24, and a length of about 0.35 inches.

The invention additionally provides a method for producing an infusion cannula. The method comprises coating a tube with a medicinal agent embedded in a polymer matrix, wherein the tube comprises an elastomeric material and has an external surface and, an internal lumen. In some embodiments, the coating comprises dipping the tube into the polymer matrix, or spraying or painting the polymer matrix onto the tube. The method of coating the tube can be selected so as to optimize the surface to which the coating is adhered. For example, the coating method may be adapted to obtain a cannula having a coating adhered to the internal lumen as well as to the external surface. Coating the tube by dipping, for example, can provide a cannula having a coating adhered to the internal lumen and to the external surface. The invention thus additionally provides an infusion cannula produced by the above method.

In addition, the invention provides a method for infusing a substance into a subject. The method comprises inserting a cannula of the invention into subcutaneous tissue of the subject and delivering the substance into the cannula. The substance is thereby infused into the subject through the cannula. Because the cannula of the invention comprises a tube coated with a medicinal agent in a polymer matrix, the method reduces adverse side effects of subcutaneous cannula insertion.

DETAILED DESCRIPTION

All scientific and technical terms used in this application have meanings commonly used in the art unless otherwise specified. As used in this application, the following words or phrases have the meanings specified.

As used herein, "polymer matrix" means a polymeric material into which another substance can be embedded. For example, a medicinal agent can be embedded in a polymer matrix. Under some conditions, such as contact with a biological fluid, the embedded medicinal agent is released from the polymer matrix into the biological fluid and/or surrounding tissues.

As used herein, "adhered to" means stuck to or fused with such that a substance adhered to a surface remains substantially attached to or closely associated with the surface.

As used herein, "a" or "an" means at least one, and unless clearly indicated otherwise, includes a plurality.

Overview

The invention provides an infusion cannula modified to incorporate one or more medicinal agents. The infusion cannula can be used in conjunction with an infusion set, for delivery of a substance into a subject's internal tissue environment. The medicinal agent can be selected to minimize adverse effects of subcutaneous cannula placement. The infusion cannula comprises a tube 20 having an inner lumen and an external surface. The tube 20 comprises an elastomeric material, and a coating is adhered to the external surface of the tube 20, wherein the coating comprises a medicinal agent and a polymer matrix. In a preferred embodiment, the medicinal agent is embedded in the polymer matrix, and the polymer is capable of sustained release of the medicinal agent. The tube can consist essentially of a single-layer or a multi-layer tube. A tube 20 comprising a uniform material, however, is preferred. Use of a single, uniform material avoids additional manufacturing expense and reduces delamination risks associated with production of multi-layer tubing. Preferably, the tube comprises a flexible, biologically compatible elastomeric material.

Figure 1:
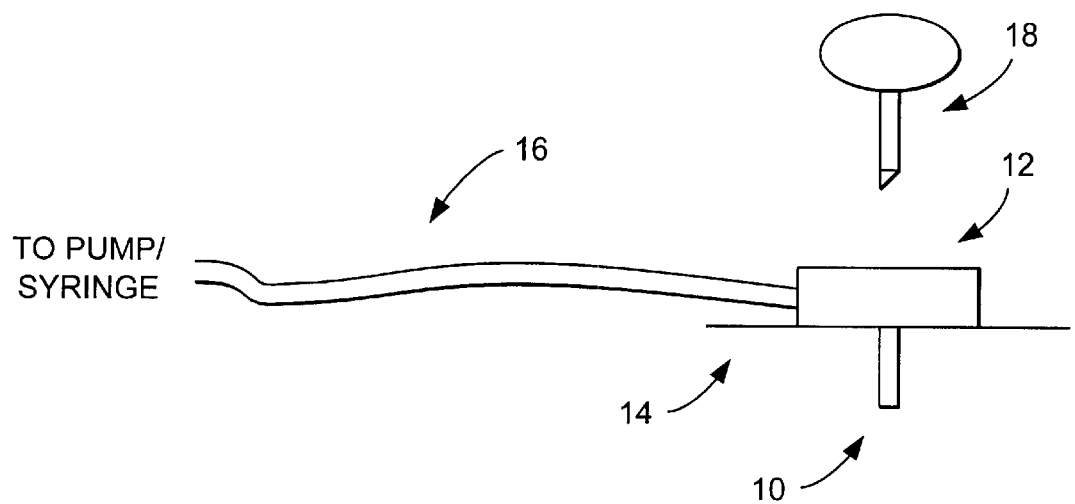
FIG. 1 is a schematic illustration of an exemplary infusion set, which can incorporate a cannula 10 of the invention.

FIG. 1 is a schematic illustration of an exemplary infusion set, which can incorporate a cannula 10 of the invention. The cannula 10 is attached to a cannula housing 12, which housing 12 is affixed to the external surface of a subject via an adhesive strip 14. Tubing 16 extends from the cannula housing to a pump or syringe that delivers the desired substance to the cannula 10 via this tubing 16. An insertion needle 18 is used to insert the cannula 10 through the subject's skin and into the underlying tissue.

Cannula

The infusion cannula of the invention preferably comprises a tube 20 having an inner lumen and an external surface. The tube 20 comprises an elastomeric material that is preferably flexible and biologically compatible. The tube 20 additionally comprises a coating adhered to the external surface of the tube 20, wherein the coating comprises a medicinal agent in a polymer matrix. Examples of elastomeric materials include, but are not limited to, polyurethane (e.g., Pellethane™, Dow Chemical Company, Midland, Mich., polytrea, polyether(amide), PEBA (PEBAX™, Elf Atochem North America, Inc., Philadelphia, Pa.), thermoplastic elastomeric olefin (TEO), copolyesters (COPs), styrenic thermoplastic elastomer (e.g., Kraton™, GLS Corporation, McHenry, Ill.), silicone, or polyvinyl chloride (PVC). The elastomeric material is preferably selected so as to be sufficiently flexible and kink-resistant to accommodate the subcutaneous placement procedure without being so rigid as to damage subcutaneous tissues and organs. Biologically compatible elastomeric materials minimize irritation and inflammation of biological tissues. In addition, compatibility between the elastomeric material and the substance to be delivered through the cannula should be taken into account. For example, polyolefin has been found to be more suitable for insulin delivery than PVC.

In one embodiment, the tube 20 comprises an inner layer of polyolefin adhered to an outer layer of PVC adhered to one another by an interlayer of adhesive, such as ethylene-vinyl acetate. This multi-layer tube combines the reduced binding, clogging, leaching and carbon dioxide penetration of polyolefin with the kink resistance and strength of PVC. Preferably, however, the elastomeric material is selected so as to achieve the desired properties with a single, uniform material to avoid having to adhere one material to another. In one embodiment, the elastomeric material comprises polyurethane. Examples of polyurethane include Pellethane™ 2363-55D and 2363-90AE (Dow Chemical Company, Midland, Mich.), which are approved for use with class III devices, suitable for use in infusion sets, and compatible with insulin.

Typical cannulae for subcutaneous placement and delivery have a gauge sufficiently large to permit passage of the desired substance through the lumen and sufficiently small to minimize trauma to surrounding tissues, with a gauge of about 24 being preferred. A typical cannula is about 0.35 inches in length. Other diameters, thicknesses and cannula shapes can be employed, so long as they are capable of delivering the desired substance into the appropriate location or tissue.

Medicinal Agents

The medicinal agent to be incorporated into a polymer matrix for the coating of the cannula is selected in accordance with the desired effect. For example, the objective may be to prevent or minimize inflammation or microbial infection. In a preferred embodiment, the polymer is capable of sustained release of the medicinal agent.

Examples of medicinal agents include, but are not limited to, anti-inflammatory, anti-bacterial, anti-viral and disinfecting agents, such as dexamethasone, cefazolin, and benzalkonium chloride. In some embodiments, the medicinal agent may be a material that kills growing cells such as microbial organisms or reactive cells that may obstruct delivery of a substance through the cannula. Suitable antiproliferative agents include, for example, silver, platinum-silver, and copper. Each of these materials has a toxic effect on growing cells, while remaining safe for internal use. Silver, salts of silver (e.g., Ag $NO_3$) and platinum-silver, for example, are oligodynamic materials, that is, they are effective as sterilizing agents in small quantities.

The use of anti-proliferative materials as the medicinal agent minimizes the possibility of obstruction due to omentum overgrowth, tissue ingrowth, and/or other body cell accumulation. Further, by providing for an anti-proliferative material within the cannula, this invention also minimizes the likelihood that bacteria will grow and accumulate within the subcutaneous reservoir of the cannula. The invention therefore provides a method for minimizing cannula obstruction while maintaining the structural integrity of the cannula.

Polymer Matrix

The coating of the cannula comprises a medicinal agent and a polymer matrix, preferably wherein the medicinal agent is embedded in the polymer matrix. In a preferred embodiment, the polymer is capable of sustained release of the medicinal agent. Exemplary constituents of a polymer matrix include, but are not limited to, diisocyanates, diamines, diols, polyols, hydrophilic polymers, and siloxane polymers. In some embodiments, the coating compound further comprises a solvent, such as tetrahydrofuran (THF) and/or isopropyl alcohol. The polymer for use in the coating can be selected to adjust the rate of release of the medicinal agent. For example, the greater the hydrophobicity of the polymer, the slower the release rate. In one embodiment, room temperature vulcanizing (RTV) silicone is used to coat a silicone cannula. In a preferred embodiment, the polymer matrix comprises polyurea (see, e.g., U.S. Pat. Nos. 5,777,060 and 5,786,439). A preferred coating material comprises polyurea, such as glucose limiting polymer (GLP; MiniMed, Inc., Sylmar, Calif.), and is prepared using THF as a solvent. The GLP typically is about 6.5 to about 8.5 percent of the polymer coating solution, with the balance comprising THF and the medicinal agent. In one example, the GLP is about 7.5%, the medicinal agent comprises dexamethasone, about 0.91–0.93%, and the balance is THF.

Other formulations of the polymer matrix can be selected in accordance with the desired use. For example, U.S. Pat. Nos. 5,777,060 and 5,786,439 describe coatings suitable for use with biosensors, particularly for use with glucose oxidase and glucose detection. These coatings share features in common with GLP, and can be adapted for use with an infusion cannula.

Methods

Figure 2:
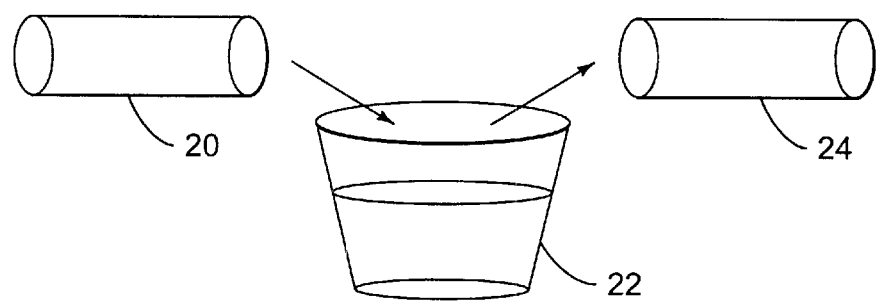
FIG. 2 is a schematic illustration of a tube 20 being dip-coated in a vat 22 containing a polymer matrix that comprises a medicinal agent, resulting in a coated tube 24, in accordance with one embodiment of the invention.

The invention additionally provides a method for producing an infusion cannula. The method comprises coating a tube 20 with a medicinal agent and a polymer matrix. The medicinal agent can be combined with the polymer matrix prior to the coating such that the medicinal agent is embedded in the polymer matrix to facilitate sustained release of the medicinal agent from the coated tube 24. The tube 20 comprises an elastomeric material, preferably a flexible, biologically compatible elastomeric material. In some embodiments, the coating comprises dipping the tube into the polymer matrix, or spraying or painting the polymer matrix onto the tube. Dipping the tube 20 into the polymer matrix is preferred when it is desirable to coat the internal lumen of the cannula with the medicinal agent. The medicinal agent can then be co-delivered with the substance to be delivered via the infusion cannula. FIG. 2 provides a schematic illustration of a tube 20 being dipped into a vat 22 containing a medicinal agent in a polymer matrix in liquid form. The resulting coated tube 24 is then dried. The coated tube 24 can be air dried or vacuum dried. Preferably the coated tube 24 is vacuum dried at about 50° C. Those skilled in the art will appreciate a variety of manners by which the tube can be coated and dried. The invention additionally provides an infusion cannula produced by the above method.

In addition, the invention provides a method for infusing a substance into a subject. The method comprises inserting a cannula of the invention into subcutaneous tissue of the subject and delivering the substance into the cannula. The substance is thereby infused into the subject through the cannula. Because the cannula of the invention comprises a medicinal agent in a polymeric material coated onto its external surface, the method offers advantages over known methods of infusing a substance into a subject. The method provides more efficient and effective substance delivery because of reduced inflammation and/or infection of the subcutaneous tissues. The minimization of inflammation, infection or other unwanted side effects provides improved control over substance delivery. The method is particularly suited for subjects requiring repeated and/or continuous infusion of a substance, such as insulin for diabetics.

EXAMPLES

The following examples are presented to illustrate the present invention and to assist one of ordinary skill in making and using the same. The examples are not intended in any way to otherwise limit the scope of the invention.

Example 1

Film Thickness and Adhesion As a Function of Polymer Coating Solution Formulation In this example, various formulations of a polymer coating solution were applied to polyurethane (PU) tubing to determine film thickness and resistance to delamination. The results are presented in Table 1. The polymer was glucose limiting polymer (GLP; lot number SD2756) from MiniMed, Inc., Sylmar, Calif. The PU tubing was Pellethane 2383-55D, 0.01×0.03 inch. Dip coating was used as the coating method and the coated tubing was vacuum dried at 50° C. Adhesion testing consisted of immersing coated PU tubing in PBS at room temperature for 3 days. The tubing was then inspected under a microscope for delamination. In addition, the coated tubing was subjected to a finger twisting test and a pulling test. In these tests, a piece of coated tubing was held between the fingers of the tester's two hands and either twisted or pulled prior to inspection. Using scanning electron microscopy, delamination appears as film separated from the tubing or as a gap.

The greatest film thickness (>0.01 mm) and least delamination were observed with polymer formulations containing 6.68–8.0 % GLP, 92.0–93.32 % THF and no ethanol, as shown in Table 1.

TABLE 1

| Sample No. | GLP | THF | ETOH | Film Thickness | Finger Twisting Test | Pulling Test |
|---|---|---|---|---|---|---|
| 1 | 8.56% | 62.75% | 28.69% | 0.0090 mm | Some delamination | Delamination |
| 2 | 7.72% | 56.60% | 35.68% | 0.0057 mm | Little delamination | Delamination |
| 3 | 6.66% | 48.86% | 44.48% | 0.0042 mm | No delamination | Delamination |
| 4 | 8.00% | 92.00% | 0 | 0.0197 mm | No delamination | Little delamination |
| 5 | 7.50% | 92.50% | 0 | 0.0150 mm | No delamination | Trace delamination |
| 6 | 6.68% | 93.32% | 0 | 0.0108 mm | No delamination | Trace delamination |

Example 2
Rate of Dexamethasone Release from Coated Tubing

In this example, polymer formulations including dexamethasone (DXMS) as a medicinal agent were tested for DXMS release from coated tubing.

Figure 3:
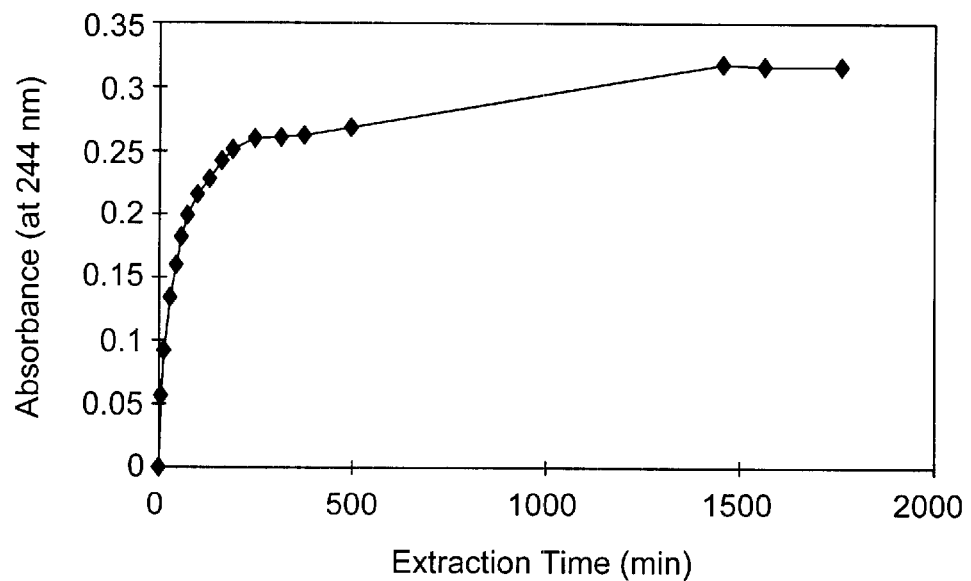
FIG. 3 is a graph showing cumulative dexamethasone (DXMS) release into phosphate buffered saline (PBS) from a tube coated with glucose limiting polymer (GLP) containing DXMS dissolved into tetrahyrdrofuran (THF). Following evaporation of the solvent, DXMS is measured by exposure to a PBS solution and monitoring dissolution via UV spectroscopy. Release is plotted as absorbance at 244 nm as a function of time in minutes. The weight of the coating layer is 0.0035 g; coating comprises 91.58% THF, 7.51% GLP, and 0.91% DXMS; coating film thickness is 22.43 $\mu$m; DXMS loaded is 0.04915 mg/cm.
Figure 4:
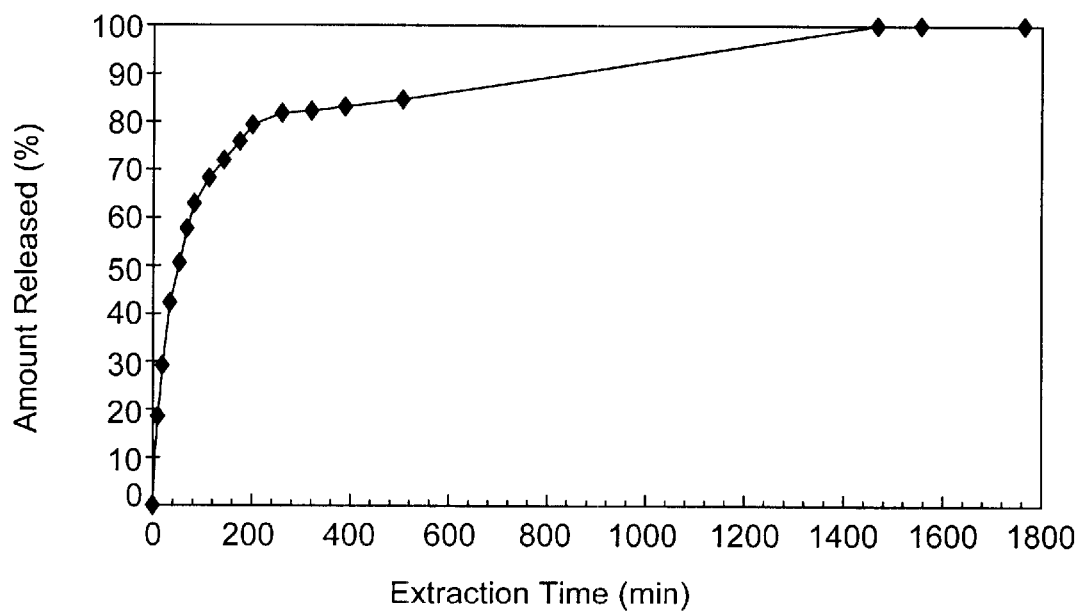
FIG. 4 is a graph showing cumulative DXMS release into PBS from a tube coated with GLP containing DXMS dissolved into THF as shown in FIG. 3. Release is plotted as percent total amount released as a function of time in minutes.

In a first experiment, the weight of the coating layer was 0.0035 g. The coating comprised 91.58% THF, 7.51% GLP, and 0.91% DXMS. Without considering the THF, the composition was 89.16% GLP and 10.84% DXMS. The thickness of the resulting film coating was 22.43 μm. DXMS was loaded at 0.04915 mg/cm. The extraction was performed without agitation. FIG. 3 is a graph showing cumulative DXMS release into phosphate buffered saline (PBS) from a tube coated with this formulation of GLP with DXMS and THF. Release is plotted as absorbance at 244 nm as a function of time in minutes. FIG. 4 is a graph showing cumulative DXMS release into PBS from a tube coated with GLP containing DXMS and THF as shown in FIG. 3. Release is plotted as percent total amount released as a function of time in minutes.

Figure 5:
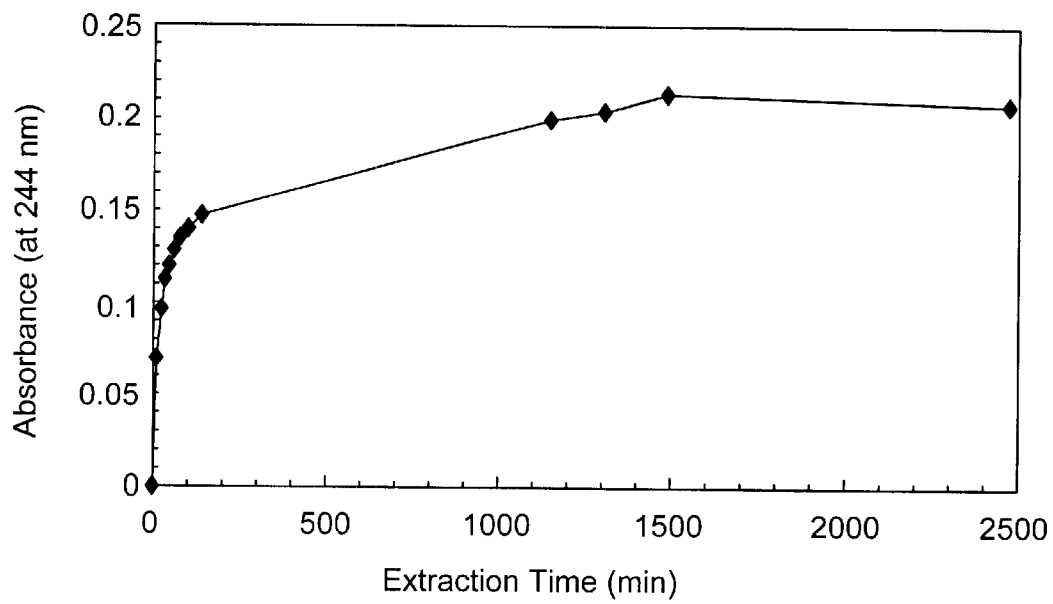
FIG. 5 is a graph showing cumulative DXMS release into PBS from a tube coated with GLP containing DXMS dissolved into THF and ethanol (ETOH). Release is plotted as absorbance at 244 nm as a function of time in minutes. The coating comprises 68.57% THF, 7.56% GLP, 0.93% DXMS and 22.94% ETOH; coating film thickness is 12.40 $\mu$m; DXMS loaded is 0.0244 mg/cm.
Figure 6:
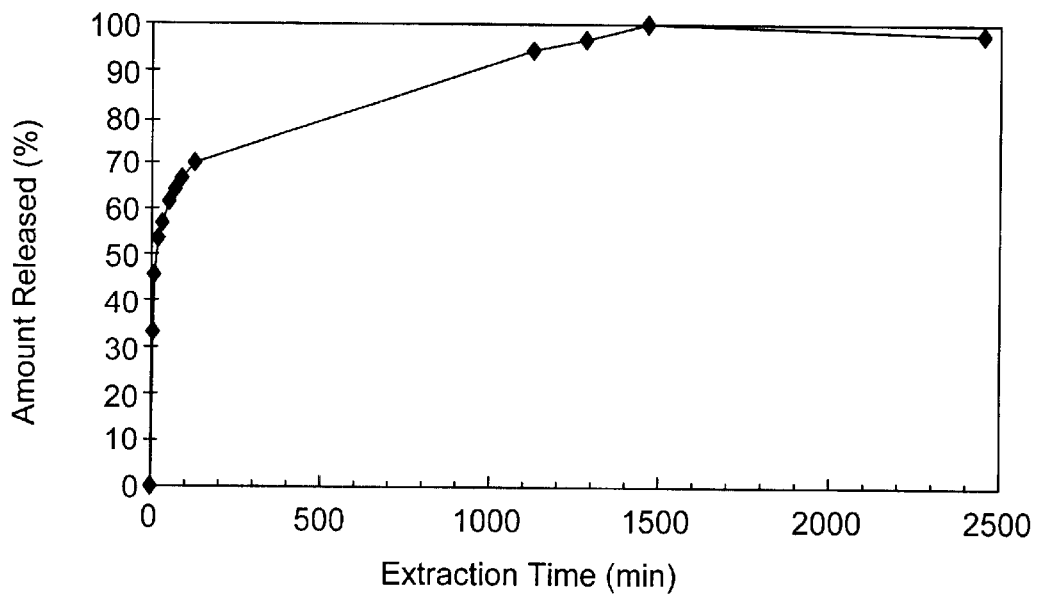
FIG. 6 is a graph showing cumulative DXMS release into PBS from a tube coated with GLP containing DXMS, THF and ETOH as shown in FIG. 4. Release is plotted as percent total amount released as a function of time in minutes.

In a second experiment, ethanol (ETOH) was added to the coating. The coating comprised 68.57% THF, 7.56% GLP, 0.93% DXMS and 22.94% ETOH. Without considering the THF and ETOH, the composition was 89.01% GLP and 10.99% DXMS. The resulting film coating had a thickness of 12.40 μm. DXMS was loaded at 0.0244 mg/cm. FIG. 5 is a graph showing cumulative DXMS release into PBS from a tube coated with GLP containing DXMS, THF and ETOH. Release is plotted as absorbance at 244 nm as a function of time in minutes. FIG. 6 is a graph showing cumulative DXMS release into PBS from a tube coated with GLP containing DXMS, THF and ETOH as shown in FIG. 5. Release is plotted as percent total amount released as a function of time in minutes.

Figure 7:
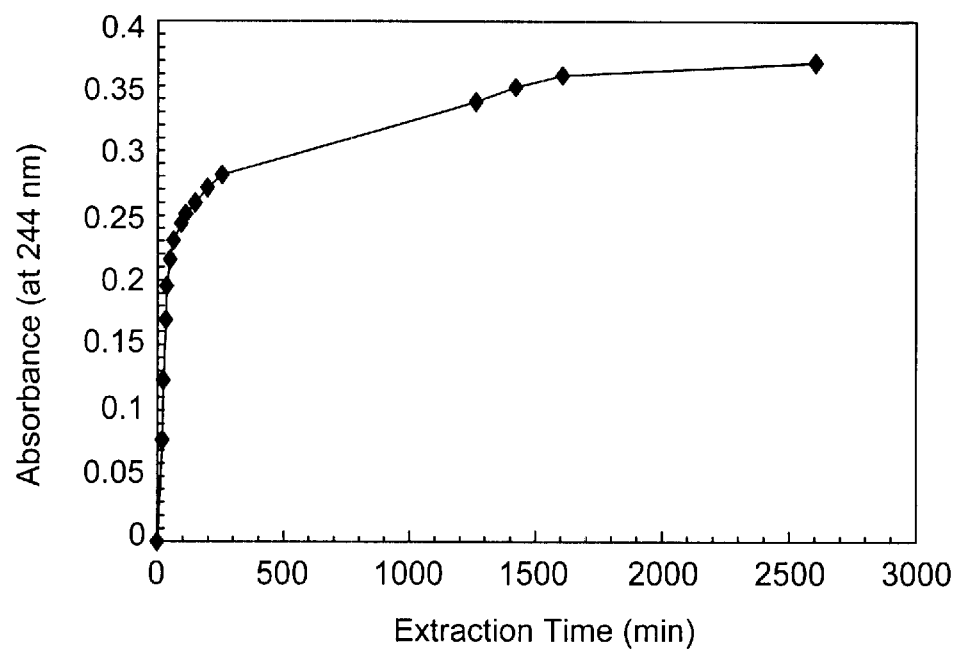
FIG. 7 is a graph showing cumulative DXMS release into PBS from a tube coated with GLP containing DXMS and THF. Release is plotted as absorbance at 244 nm as a function of time in minutes. The coating comprises 91.58% THF, 7.51% GLP, and 0.91% DXMS; coating film thickness is 25.27 μm; DXMS loaded is 0.04915 mg/cm.
Figure 8:
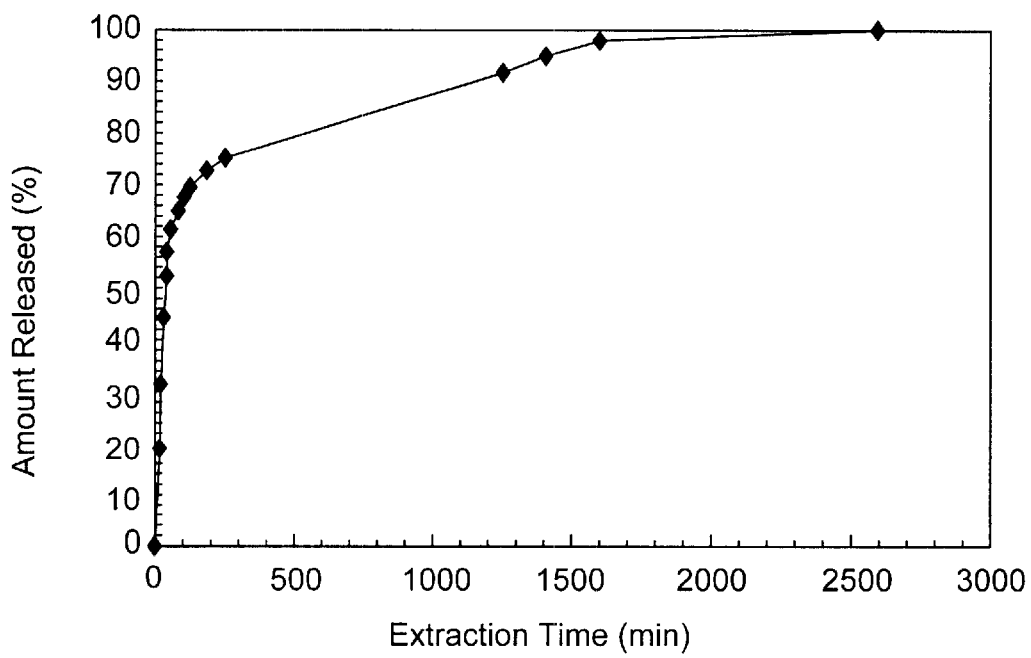
FIG. 8 is a graph showing cumulative DXMS release into PBS from a tube coated with GLP containing DXMS and THF as shown in FIG. 7. Release is plotted as percent total amount released as a function of time in minutes.

In a third experiment, the same formulation as in the first experiment was used, but with a greater film thickness. The coating comprised 91.58% THF, 7.51% GLP, and 0.91% DXMS. The thickness of the resulting film coating was 25.27 μm. DXMS was loaded at 0.04915 mg/cm. FIG. 7 is a graph showing cumulative DXMS release into PBS from a tube coated with GLP containing DXMS and THF at this greater thickness. Release is plotted as absorbance at 244 nm as a function of time in minutes. FIG. 8 is a graph showing cumulative DXMS release into PBS from the more thickly coated tube as shown in FIG. 7. Release is plotted as percent total amount released as a function of time in minutes.

The foregoing description of preferred embodiments of the invention has been presented for the purposes of illustration and description. It is not intended to be exhaustive or to limit the invention to a precise form disclosed. Many modifications and variations are possible in light of the above teaching. It is intended that the scope of the invention be limited not by this detailed description, but rather by the claims appended hereto.

What is claimed is:

1. An infusion cannula comprising:

(a) a tube having an inner lumen and an external surface, wherein the tube comprises an elastomeric material; and (b) a coating adhered to the external surface of the tube, wherein the coating comprises a medicinal agent and a polymer matrix, wherein the polymer matrix comprises polyurea, and wherein the coating is prepared from a solution comprising 6.5 to 8.5% polymer, about 0.91 to 0.93% medicinal agent, and a solvent.

2. The infusion cannula of claim 1, wherein the medicinal agent is embedded in the polymer matrix and the polymer matrix is capable of sustained release of the medicinal agent.

3. The infusion cannula of claim 1, wherein the elastomeric material comprises polyurethane, polyether(amide), polyester, PEBA, thermoplastic elastomeric olefin, copolyester, styrenic thermoplastic elastomer, or polyamide.

4. The infusion cannula of claim 1, wherein the elastomeric material comprises polyurethane or polyurea.

5. The infusion cannula of claim 1, wherein the polymer matrix further comprises a diisocyanate.

6. The infusion cannula of claim 5, wherein the polymer matrix further comprises a siloxane polymer.

7. The infusion cannula of claim 5, wherein the polymer matrix further comprises a chain extender.

8. The infusion cannula of claim 1, wherein the coating is prepared from a solution comprising about 7.5% polymer and about 0.91% dexamethasone.

9. The infusion cannula of claim 1, wherein the solvent comprises tetrahydrofuran.

10. The infusion cannula of claim 1, wherein the tube has a gauge of about 24.

11. The infusion cannula of claim 1, wherein the tube has a length of about 0.35 inches.

12. The infusion cannula of claim 1, wherein the medicinal agent comprises an anti-inflammatory, anti-bacterial, anti-viral, anti-proliferative, or disinfecting agent.

13. The infusion cannula of claim 1, wherein the medicinal agent is selected from the group consisting of dexamethasone, cefazolin, benzalkonium chloride, silver or a salt thereof, silver-platinum, copper, and acyclovir.

14. The infusion cannula of claim 1, wherein the coating, exclusive of solvent, comprises about 89.16% polymer and about 10.84% dexamethasone.

15. A method for producing an infusion cannula comprising coating an elastomeric tube with a polymer matrix, wherein the polymer matrix comprises a medicinal agent.

16. The method of claim 15, wherein the coating comprises dipping the elastomeric tube into the polymer matrix.

17. The method of claim 15, wherein the coating comprises spraying or painting the polymer matrix onto the tube.

18. An infusion cannula produced by the method of claim 15.

19. A method for infusing a substance into a subject comprising inserting the cannula of claim 1 into subcutaneous tissue of the subject and delivering the substance into the cannula.

20. The infusion cannula of claim 1 wherein the coating is prepared from a solution that does not include ethanol.

* * * * *

UNITED STATES PATENT AND TRADEMARK OFFICE
CERTIFICATE OF CORRECTION

PATENT NO.    : 6,475,196 B1
DATED         : November 5, 2002
INVENTOR(S)   : David J. Vachon It is certified that error appears in the above-identified patent and that said Letters Patent is hereby corrected as shown below:

<u>Title page,</u>
Item [56], References Cited, U.S. PATENT DOCUMENTS, insert

| | | |
|---|---|---|
| -- 4,557,724 | 12/1985 | Gregonis et al. |
| 4,559,033 | 12/1985 | Stephen et al. |
| 4,562,751 | 01/1986 | Nason et al. |
| 4,592,920 | 06/1986 | Murtfeld |
| 4,678,408 | 07/1987 | Nason et al. |
| 4,685,903 | 08/1987 | Cable et al. |
| 4,755,173 | 07/1988 | Konopka et al. |
| 4,781,675 | 11/1988 | White |
| 5,176,662 | 01/1993 | Bartholomew et al. |
| 5,257,980 | 11/1993 | Van Antwerp et al. |
| 5,522,803 | 06/1996 | Teissen-Simon |
| 5,584,813 | 12/1996 | Livingston et al. |
| 5,777,060 | 07/1998 | Van Antwerp |
| 5,786,439 | 07/1998 | Van Antwerp et al. -- |

FOREIGN PATENT DOCUMENTS, insert

| | | |
|---|---|---|
| -- 0 328 421 A2 | 08/16/89 | Europe |
| 0 799 623 A2 | 10/08/97 | Europe |
| WO 84/01102 | 03/29/84 | PCT |
| WO 84/01721 | 05/10/84 | PCT |
| WO 86/02006 | 04/10/86 | PCT |
| WO 93/11821 | 06/24/93 | PCT |
| WO 95/04568 | 02/16/95 | PCT |
| WO 98/19627 | 05/14/98 | PCT |
| WO 99/32168 | 07/01/99 | PCT -- |

Item [57], ABSTRACT,
Line 2, "of" should read -- or --.

UNITED STATES PATENT AND TRADEMARK OFFICE
CERTIFICATE OF CORRECTION

PATENT NO. : 6,475,196 B1
DATED : November 5, 2002
INVENTOR(S) : David J. Vachon It is certified that error appears in the above-identified patent and that said Letters Patent is hereby corrected as shown below:

<u>Column 9,</u>
Line 6, after "agent", strike the period (".") and replace with a comma -- , -- and insert -- wherein the coating comprises dipping the elastomeric tube into the polymer matrix, or spraying or painting the polymer matrix onto the tube. --

Signed and Sealed this

Nineteenth Day of August, 2003

JAMES E. ROGAN
*Director of the United States Patent and Trademark Office*